(12) United States Patent
Kim et al.

(10) Patent No.: US 12,262,860 B2
(45) Date of Patent: Apr. 1, 2025

(54) DISHWASHER

(71) Applicant: SAMSUNG ELECTRONICS CO., LTD., Suwon-si (KR)

(72) Inventors: Jusik Kim, Suwon-si (KR); Johannes Büsing, Suwon-si (KR); Hyeoneui Choi, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 18/151,202

(22) Filed: Jan. 6, 2023

(65) Prior Publication Data

US 2023/0157517 A1 May 25, 2023

Related U.S. Application Data

(63) Continuation of application No. PCT/KR2021/006325, filed on May 21, 2021.

(30) Foreign Application Priority Data

Jul. 6, 2020 (KR) .................. 10-2020-0083092

(51) Int. Cl.
*A47L 15/50* (2006.01)
*A61M 16/18* (2006.01)

(52) U.S. Cl.
CPC ........... *A47L 15/503* (2013.01); *A47L 15/501* (2013.01); *A47L 15/507* (2013.01); *A61M 16/18* (2013.01)

(58) Field of Classification Search
CPC ...... A47L 15/18; A47L 15/501; A47L 15/503; A47L 15/504; A47L 15/505; A47L 15/507
See application file for complete search history.

(56) References Cited

U.S. PATENT DOCUMENTS 3,752,322 A * 8/1973 Fiocca .................. A47L 15/505
211/41.8
4,917,248 A * 4/1990 Friskney ............... A47L 15/503
211/184
(Continued)

FOREIGN PATENT DOCUMENTS

CH 694033 A5 6/2004
EP 1413241 A1 4/2004
(Continued)

OTHER PUBLICATIONS

International Search Report and Written Opinion of the International Searching Authority dated Sep. 17, 2021, in connection with International Application No. PCT/KR2021/006325, 9 pages.
(Continued)

*Primary Examiner* — Patrick D Hawn

(57) ABSTRACT

Disclosed herein is including a basket including an improved dish support structure. The dishwasher includes a basket provided to accommodate dishes. The basket includes a basket body, an upper holder frame including one end supporting a portion of the dish and the other end rotatably coupled to the basket body, and a lower holder frame including one end supporting the other portion of the dish supported by the upper holder frame, and the other end rotatably coupled to the basket body. A distance between one end of the upper holder frame and one end of the lower holder frame is adjusted as one of the upper holder frame and the lower holder frame is rotated.

18 Claims, 18 Drawing Sheets

(56) References Cited

U.S. PATENT DOCUMENTS

| | | | |
|---|---|---|---|
| 6,848,585 B2 * | 2/2005 | VanLandingham | A47L 15/503 211/41.9 |
| 7,766,175 B2 * | 8/2010 | Jadhav | A47L 15/505 211/41.9 |
| 7,931,155 B2 * | 4/2011 | Bastuji | A47L 15/503 211/41.9 |
| 8,104,628 B2 * | 1/2012 | Kim | A47L 15/503 211/171 |
| 8,540,085 B2 | 9/2013 | Klump et al. | |
| 8,651,287 B2 * | 2/2014 | Moser | A47L 15/503 211/195 |
| 8,701,898 B2 | 4/2014 | Chai | |
| 8,714,371 B2 | 5/2014 | Haider | |
| 8,757,419 B2 * | 6/2014 | Schessl | A47L 15/503 220/489 |
| 9,119,524 B2 * | 9/2015 | Renz | A47L 15/503 |
| 10,165,927 B2 | 1/2019 | Mesa et al. | |
| 10,405,731 B2 * | 9/2019 | Harr | A47L 15/503 |
| 10,463,226 B2 | 11/2019 | Mesa et al. | |
| 10,791,906 B2 * | 10/2020 | Feddema | A47L 15/504 |
| 11,006,814 B1 * | 5/2021 | Simmonds | A47L 15/505 |
| 11,330,961 B1 * | 5/2022 | Rowe | A47L 15/505 |
| 11,642,002 B1 * | 5/2023 | Tanpure | A47L 15/503 211/41.8 |
| 11,826,004 B2 * | 11/2023 | Reiter | A47L 15/503 |
| 2005/0109378 A1 | 5/2005 | Landsiedel et al. | |
| 2007/0039904 A1 * | 2/2007 | Purushothaman | A47L 15/504 211/41.8 |
| 2012/0056519 A1 | 3/2012 | Woo et al. | |
| 2013/0299438 A1 | 11/2013 | McDaniel et al. | |
| 2020/0008648 A1 | 1/2020 | Feddema et al. | |
| 2020/0329947 A1 * | 10/2020 | Clerkin | A47L 15/4278 |

FOREIGN PATENT DOCUMENTS

| | | |
|---|---|---|
| EP | 2554100 A2 | 2/2013 |
| EP | 2096979 B1 | 7/2018 |
| EP | 3705017 A1 | 9/2020 |
| JP | 3799731 B2 | 7/2006 |
| KR | 10-1996-0020931 A | 6/1996 |
| KR | 1996-0013162 B1 | 9/1996 |
| KR | 20-0272336 Y1 | 4/2002 |
| KR | 10-2005-0122353 A | 12/2005 |
| KR | 10-2008-0078123 A | 8/2008 |
| KR | 10-2011-0092320 A | 8/2011 |
| KR | 10-1154957 B1 | 6/2012 |
| KR | 10-2012-0107398 A | 10/2012 |
| KR | 10-1290375 B1 | 7/2013 |
| KR | 10-1366286 B1 | 2/2014 |
| KR | 10-1397034 B1 | 5/2014 |
| WO | 2013045543 A1 | 4/2013 |

OTHER PUBLICATIONS

Supplementary European Search Report dated Oct. 30, 2023, in connection with European Patent Application No. 21838124.2, 8 pages.

* cited by examiner

DISHWASHER

CROSS-REFERENCE TO RELATED APPLICATIONS

This application is a continuation application, under 35 U.S.C. § 111(a), of international application No. PCT/KR2021/006325, filed on May 21, 2021, which claims priority to Korean Patent Application No. 10-2020-0083092, filed on Jul. 6, 2020, in the Korean Intellectual Property Office, the disclosure of which is incorporated by reference herein in its entirety.

BACKGROUND

1. Field

The disclosure relates to a dishwasher, and more particularly, to a dishwasher including a basket including an improved dish support structure.

2. Description of Related Art

A dishwasher is a device that automatically removes food residues on dishes using detergent and washing water.

The dishwasher includes a housing forming an exterior, a washing chamber formed by a tub arranged inside the housing, a door configured to open and close the washing chamber, a storage container arranged inside the washing chamber to accommodate dishes, and an arm assembly configured to spray washing water to the storage container.

The storage container including a basket may require a support member to support the dishes and prevent the dishes from shaking during a washing process.

SUMMARY

Therefore, it is an aspect of the disclosure to provide a dishwasher including a basket provided with a support structure capable of stably supporting dishes even when the dishes are transferred or the dishwasher is operated.

It is another aspect of the disclosure to provide a dishwasher including a basket provided with a support structure capable of supporting various types and sizes of dishes.

Additional aspects of the disclosure will be set forth in part in the description which follows and, in part, will be obvious from the description, or may be learned by practice of the disclosure.

In accordance with an aspect of the disclosure, a dishwasher includes a basket provided to accommodate dishes. The basket includes a basket body, an upper holder frame including one end supporting a portion of a dish, and the other end rotatably coupled to the basket body, and a lower holder frame including one end supporting the other portion of the dish supported by the upper holder frame, and the other end rotatably coupled to the basket body. A distance between one end of the upper holder frame and one end of the lower holder frame is adjusted as one of the upper holder frame and the lower holder frame is rotated.

The lower holder frame may include a frame body rotatably coupled to the basket body and extending in one direction, and a plurality of support tines protruding from the frame body to support the dish and arranged in an extending direction of the frame body.

Each of the plurality of support tines may include a support member in contact with the dish to support the dish, and a plurality of bending members configured to connect the support member and the frame body. The plurality of bending members may be arranged to form a line including at least one bending point, and the plurality of bending members may be connected to each other.

The plurality of bending members may be arranged to lie on one plane, and the support member may be bent at one end of the line formed by connecting the plurality of bending members to each other, so as not to lie on the plane.

The basket may further include a rotating device fixed to the basket body and configured to rotate the lower holder frame.

The lower holder frame may further include a connection tine bent at one end of the frame body and connected to the rotating device, and the connection tine may be coupled to the rotating device.

The rotating device may include a slide button to which one end of the connection tine is coupled, and a rotating device body coupled to the basket body and including a guide rail to which the slide button is inserted and coupled.

The slide button may slide against the rotating device body along the guide rail. In response to the sliding of the slide button in one direction to adjust a distance between one end of the upper holder frame and the plurality of support tines, the slide button may press the connection tine in one direction, the frame body may be rotated by the pressure of the connection tine, and the plurality of support tines may be rotated together with the frame body.

The slide button may include a coupling rib forming a coupling groove to which one end of the connection tine is inserted and coupled. The rotating device body may include a mounting rib in which a plurality of mounting grooves is formed to allow the connection tine, which is rotated by the slide button, to be mounted thereto.

The slide button may be manually slid. In response to the completion of the sliding of the slide button, the connection tine may be mounted to one of the plurality of mounting grooves to prevent the rotation of the lower holder frame caused by a weight of the dish.

The basket may further include a binder provided to allow the lower holder frame to be rotatably coupled to the basket body.

The basket body may be formed in such a way that a plurality of wires is coupled to each other to form a grid shape. The binder may include a first binding groove into which the frame body is inserted, a second binding groove into which one of the plurality of wires parallel to the frame body is inserted, and a clamp fastened to one of the plurality of wires perpendicular to the one wire inserted into the second binding groove.

The frame body may correspond to a first frame body, and the upper holder frame may include a second frame body extending in one direction, a coupling tine connected to a side end of the second frame body and rotatably coupled to the basket body, and a holding tine protruding from the second frame body and forming a plurality of holding grooves supporting the dish.

The dish may include a wine glass. The holding groove of the upper holder frame may support a stem or a base of the wine glass, and the support tine of the lower holder frame may support the ball of the wine glass.

The dish may be arranged and supported between the plurality of support tines.

In accordance with another aspect of the disclosure, a dishwasher includes a washing chamber, a basket body arranged inside the washing chamber to accommodate dishes, and a holder frame including a plurality of support tines arranged to support the dishes and configured to be rotated with respect to the basket body. According to a rotation of the holder frame, the plurality of support tines is positioned at a first position or a second position. In response to the plurality of support tines being positioned at the first position, the plurality of support tines is arranged close to a bottom of the basket body to support the dishes placed on the basket body. In response to the plurality of support tines being positioned at the second position, the plurality of support tines is arranged further from the bottom of the basket body in comparison with the first position, so as to allow the dishes to be supported between the plurality of support tines.

The holder frame may include a frame body rotatably coupled to the basket body and extending in one direction, and the plurality of support tines may protrude from the frame body.

Each of the plurality of support tines may include an extension extending from the frame body in one direction, and a support member bent at one end of the extension to support the dishes in response to the plurality of support tines being positioned at the first position.

The holder frame may correspond to a first holder frame. The dishwasher may further include a second holder frame supporting the dishes and rotatably coupled to the basket body. One portion of the dish may be supported by the first holder frame and other portion of the dish may be supported by the second holder frame.

The dishwasher may further include a rotating device configured to rotate the holder frame. The holder frame may further include a connection tine connected to the frame body and pressed by the rotating device. The rotating device may include a slide button configured to slide to press the connection tine, and a rotating device body including a guide rail provided to guide the sliding of the slide button.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
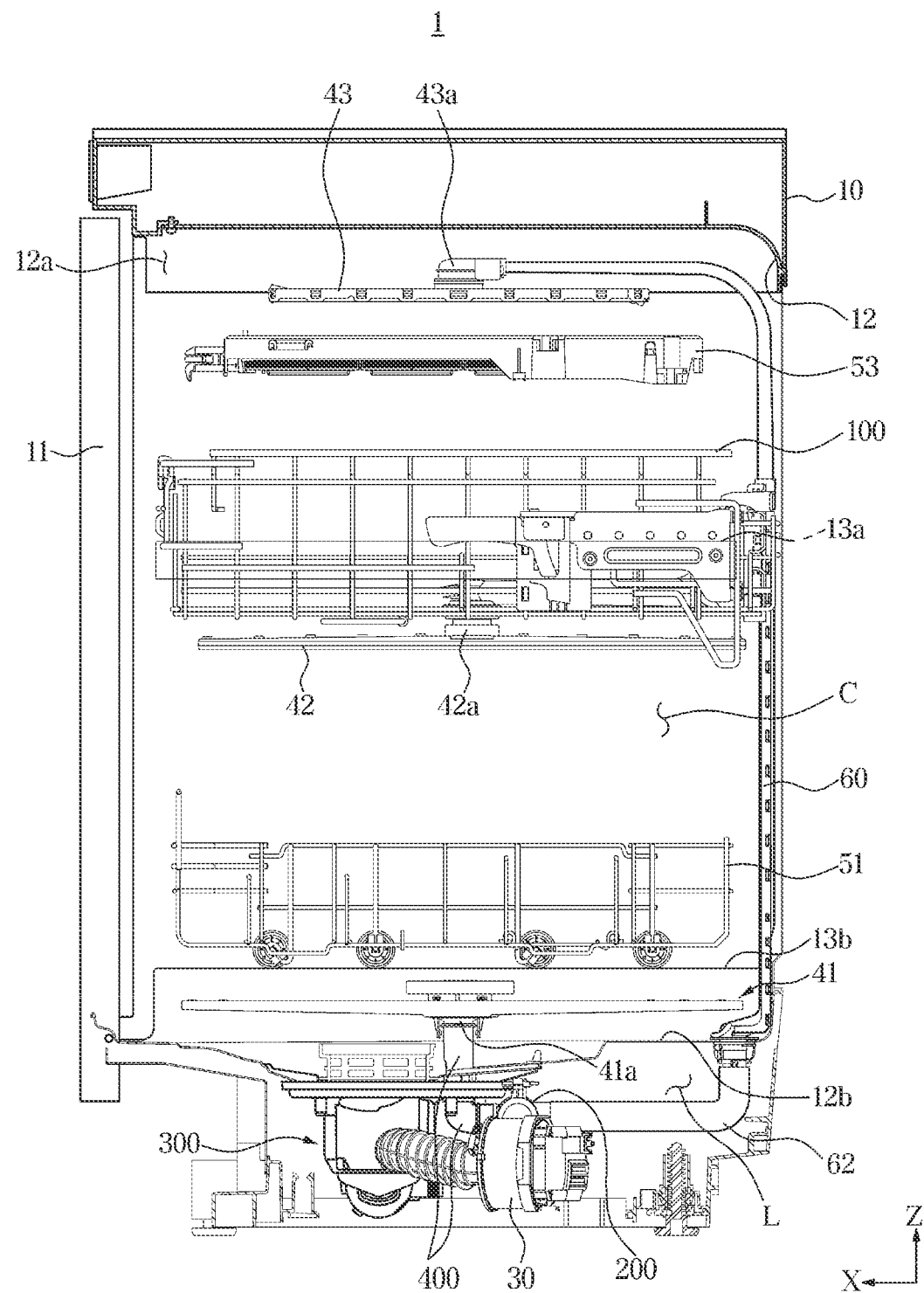
FIG. 1 is a side cross-sectional view of a dishwasher according to an embodiment of the disclosure.

FIGS. 1 through 18, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Embodiments described in the disclosure and configurations shown in the drawings are merely examples of the embodiments of the disclosure, and may be modified in various different ways at the time of filing of the present application to replace the embodiments and drawings of the disclosure.

In addition, the same reference numerals or signs shown in the drawings of the disclosure indicate elements or components performing substantially the same function.

Also, the terms used herein are used to describe the embodiments and are not intended to limit and/or restrict the disclosure. The singular forms "a," "an" and "the" are intended to include the plural forms as well, unless the context clearly indicates otherwise. In this disclosure, the terms "including", "having", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, but elements are not limited by these terms. These terms are only used to distinguish one element from another element. For example, without departing from the scope of the disclosure, a first element may be termed as a second element, and a second element may be termed as a first element. The term of "and/or" includes a plurality of combinations of relevant items or any one item among a plurality of relevant items.

In the following detailed description, the terms of "front side", "rear side", "upper portion", "lower portion", and the like may be defined by the drawings, but the shape and the location of the component is not limited by the term.

The disclosure will be described more fully hereinafter with reference to the accompanying drawings.

FIG. 1 is a side cross-sectional view of a dishwasher according to an embodiment of the disclosure.

Referring to FIG. 1, a dishwasher 1 may include a housing 10 forming an exterior thereof. The dishwasher 1 may include a tub 12 arranged inside the housing 10. The tub 12 may be formed in a substantially box shape. A front surface of the tub 12 may be opened. That is, the front surface of the tub 12 may correspond to an opening 12a.

The dishwasher 1 may include a door 11 configured to open and close the opening 12a of the tub 12. An upper portion and a lower portion of the door 11 may be hinged to the housing 10 so as to open and close the opening 12a of the tub 12. However, the disclosure is not limited thereto, a side portion of the door 11 may be hinged to the housing 10 so as to open and close the opening 12a of the tub 12. Alternatively, the door 11 may be installed in the housing 10 through an opening and closing structure rather than the hinge.

The dishwasher 1 may further include a storage container arranged in the tub 12 to accommodate dishes. The storage container may include a plurality of baskets 51, 100, and 53.

The plurality of baskets 51, 100, and 53 may be arranged in a vertical direction Z of the dishwasher 1, and correspond to a lower basket 51, a middle basket 100, and an upper basket 53 in order from bottom to top. A lower guide rack 13b may be provided to support the lower basket 51, and a middle guide rack 13a may be provided to support the middle basket 100. The upper basket 53 may be formed in the form of a rack assembly, and thus dishes having a relatively small volume may be accommodated therein. The middle guide rack 13a and the lower guide rack 13b may be installed on a side surface of the tub 12 to be slidable in a front and rear direction X toward the opening 12a of the tub 12.

However, the disclosure is not limited thereto, and the upper basket 53 may not be included according to the size of the tub 12. Accordingly, the storage container may include only the middle basket 100 and the lower basket 51.

The dishwasher 1 may include a sump 300 provided to store washing water. The dishwasher 1 may include a washing chamber C, which is a space formed by the inside of the tub 12.

The washing chamber C is a space in which dishes placed on the baskets 51, 100, and 53 may be washed by washing water and dried. The washing chamber C may be defined as an inner space of the tub 12 formed by side surfaces, a rear surface, and a lower surface 12b of the tub 12 and the sump 300 communicating with the lower surface. The washing water circulated in the washing chamber C may be discharged to the outside of the washing chamber C only through the sump 300 rather than other components.

The dishwasher 1 may include a plurality of arm assemblies 41, 42, and 43 configured to spray washing water toward the baskets 51, 100, and 53 so as to wash dishes stored in the baskets 51, 100, and 53. The arm assemblies 41, 42, and 43 may be arranged in the vertical direction Z of the dishwasher 1, and correspond to a first arm assembly 41, a second arm assembly 42, and a third arm assembly 43 in order from bottom to top. The first arm assembly 41 may be arranged under the lower basket 51, the second arm assembly 42 may be arranged under the middle basket 100, and the third arm assembly 43 may be arranged above the upper basket 53.

Particularly, the second arm assembly 42 may be fixed to a lower side of the middle basket 100, and in response to separating the middle basket 100 from the middle guide rack 13a, the second arm assembly 42 together with the middle basket 100 may be separated from a duct 60.

However, the disclosure is not limited thereto. For example, the second arm assembly 42 may be arranged above the middle basket 100. In addition, when the upper basket 53 is omitted, the third arm assembly 43 may be arranged above the middle basket 100.

The first arm assembly 41 may be configured to be rotated about a rotating shaft 41a, the second arm assembly 42 may be configured to be rotated about a rotating shaft 42a, and the third arm assembly 43 may be configured to be rotated about a rotating shaft 43a.

Unlike the second arm assembly 42 and the third arm assembly 43, the first arm assembly 41 may be fixed to one side of the sump 300 and arranged on the lower surface 12b of the tub 12. In certain embodiments, the first arm assembly may be fixed to a single side of the sump 300.

The dishwasher 1 may include a circulation pump 30 configured to pump washing water, which is stored in the sump 300, or washing water, which is introduced into the inside of the dishwasher 1 from an outside, to the arm assemblies 41, 42, and 43. The washing water pumped by the circulation pump 30 may be supplied to the first arm assembly 41 through an alternating device 200 connected to the circulation pump 30 or moved to an upper side by the duct 60 and then supplied to the second arm assembly 42 or the third arm assembly 43.

The alternating device 200 may supply washing water to the first arm assembly 41 through a connector 400 connected to the first arm assembly 41 and may supply washing water to the duct 60 through a flow path 62 connected to the duct 60.

The dishwasher 1 may include the connector 400 connecting the alternating device 200 and the first arm assembly 41. One end of the connector 400 may communicate with the alternating device 200, and the other end of the connector 400 may communicate with the first arm assembly 41. Therefore, as described above, the washing water pumped by the circulation pump 30 may be introduced into the alternating device 200, and the washing water moved to the connector 400 by the alternating device 200 may be sprayed to the lower basket 51 through the first arm assembly 41.

However, the disclosure is not limited thereto, and the circulation pump 30 may be directly connected to the connector 400 and thus the washing water pumped by the circulation pump 30 may be directly introduced to the first arm assembly 41 through the connector 400 without passing through the alternating device 200. In this case, the dishwasher 1 may not include the alternating device 200.

The dishwasher 1 may include a drain hose (not shown) provided to drain washing water remaining inside the tub 12. The drain hose may be connected to the sump 300 to drain the washing water stored in the sump 300 to the outside of the dishwasher 1.

As described above, the washing water collected in the sump 300 may be purified by a filter (not shown) inside the sump 300 and circulated back into the washing chamber C by the circulation pump 30.

In a machine room L formed in a lower portion of the dishwasher 1, the above-described configuration such as the circulation pump 30, the alternating device 200, and the sump 300 may be arranged.

Figure 2:
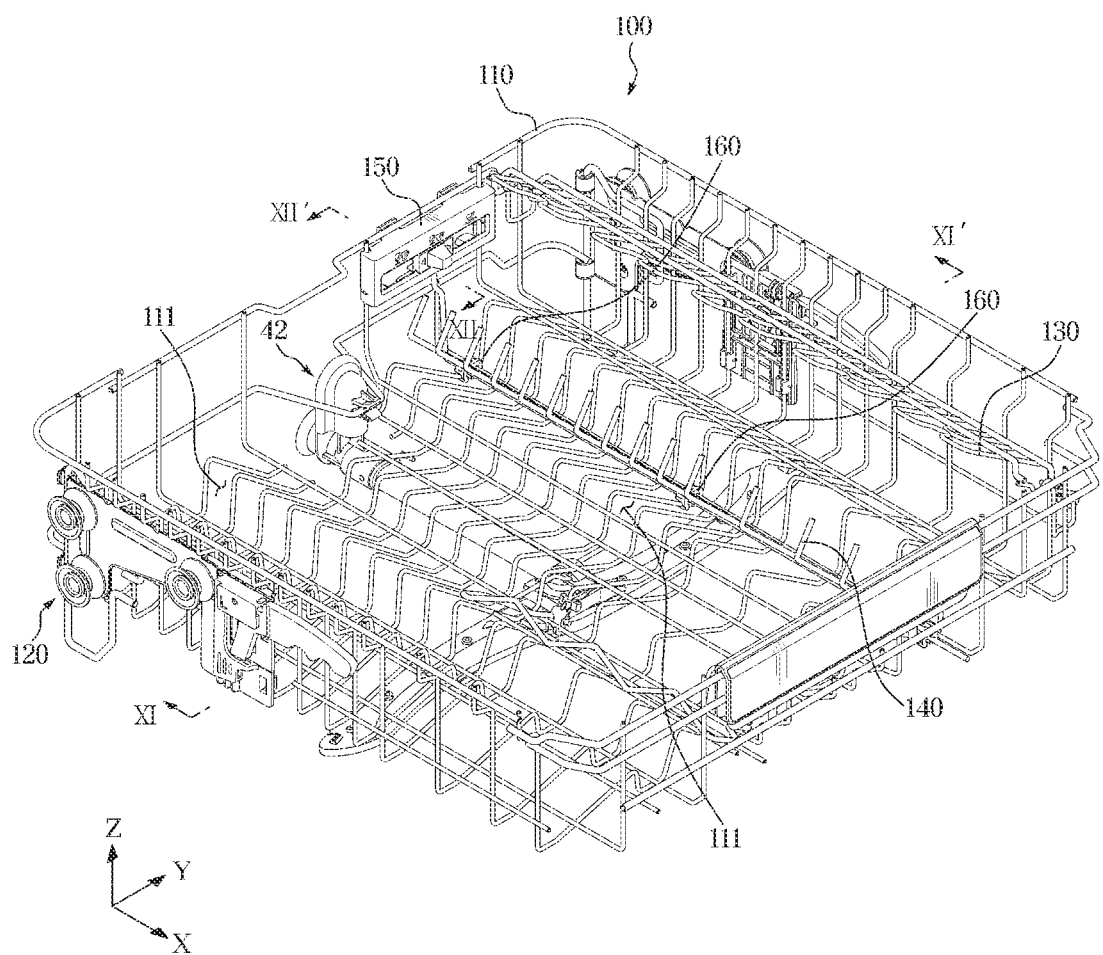
FIG. 2 is a perspective view illustrating a basket of the dishwasher shown in FIG. 1.
Figure 3:
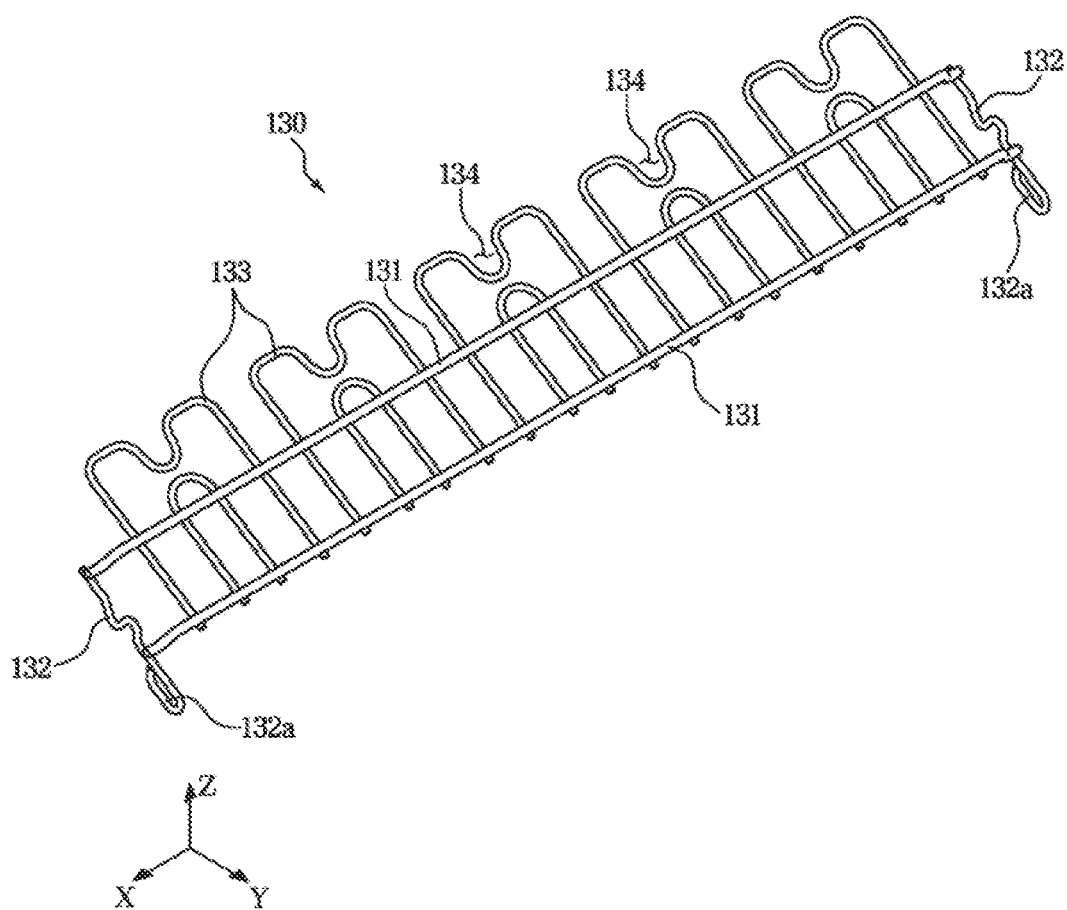
FIG. 3 is a perspective view illustrating an upper holder frame of the basket shown in FIG. 2.
Figure 4:
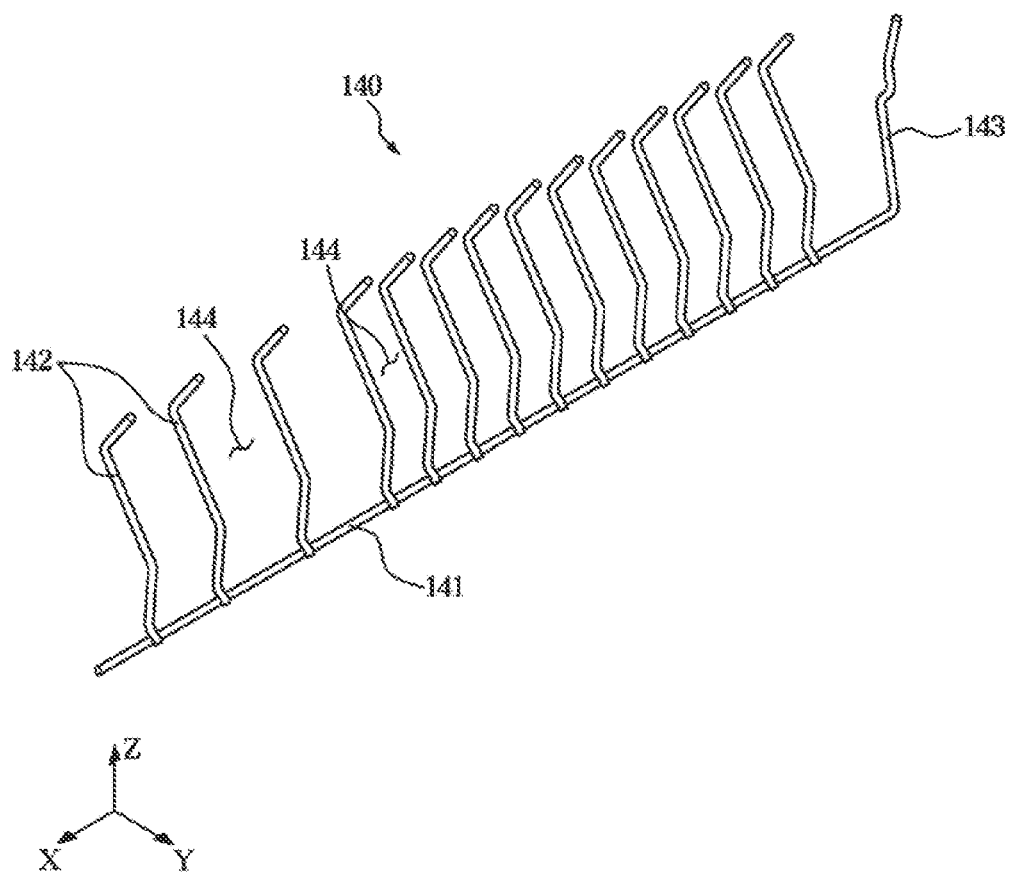
FIG. 4 is a perspective view illustrating a lower holder frame of the basket shown in FIG. 2.
Figure 5:
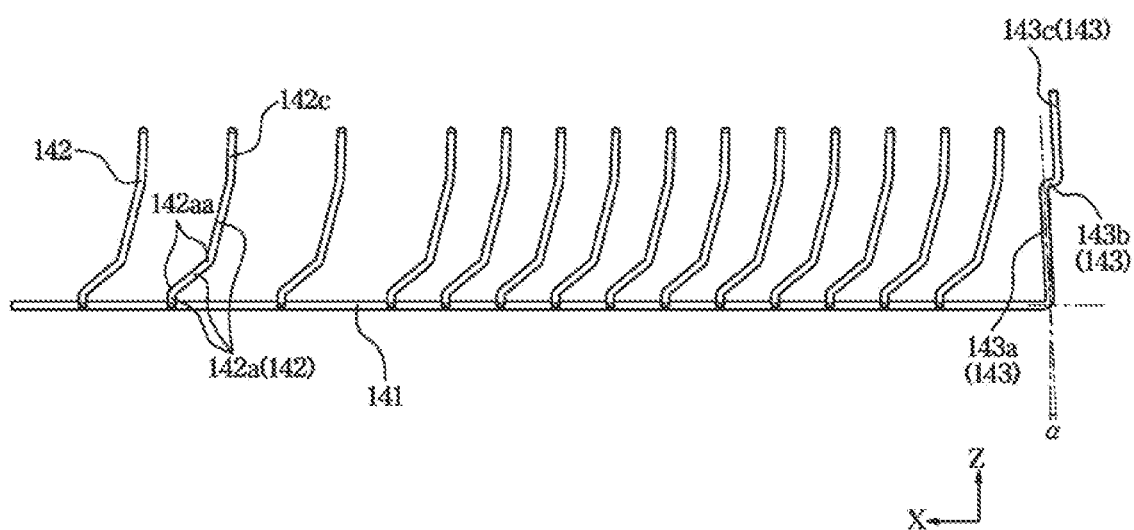
FIG. 5 is a side view illustrating the lower holder frame shown in FIG. 2.
Figure 6:
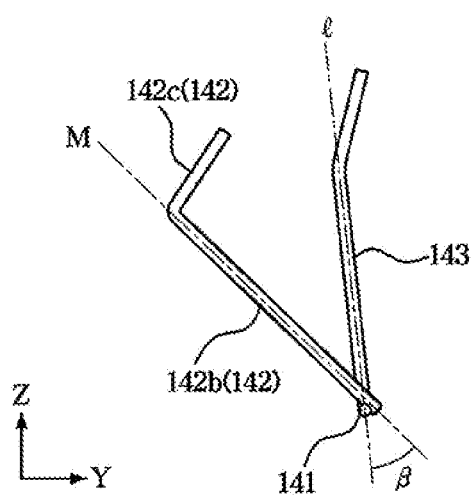
FIG. 6 is a front view illustrating the lower holder frame shown in FIG. 2.
Figure 7:
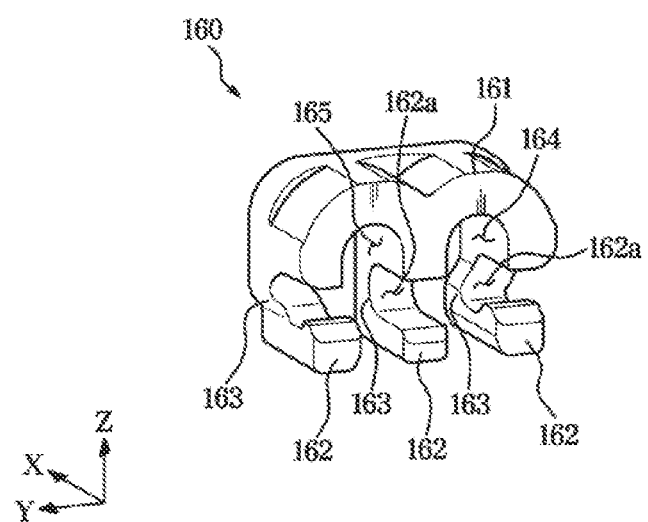
FIG. 7 is a perspective view illustrating a binder of the basket shown in FIG. 2.
Figure 8:
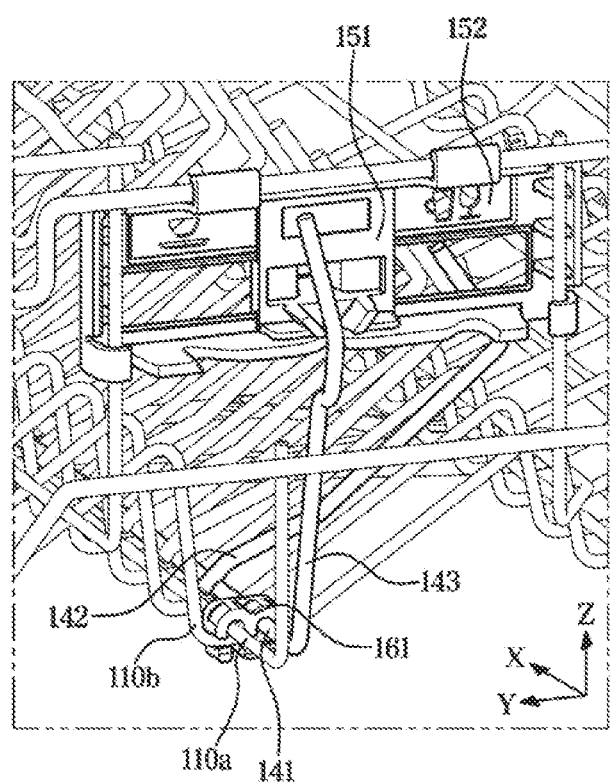
FIG. 8 is a rear view illustrating a part of the basket shown in FIG. 2.
Figure 9:
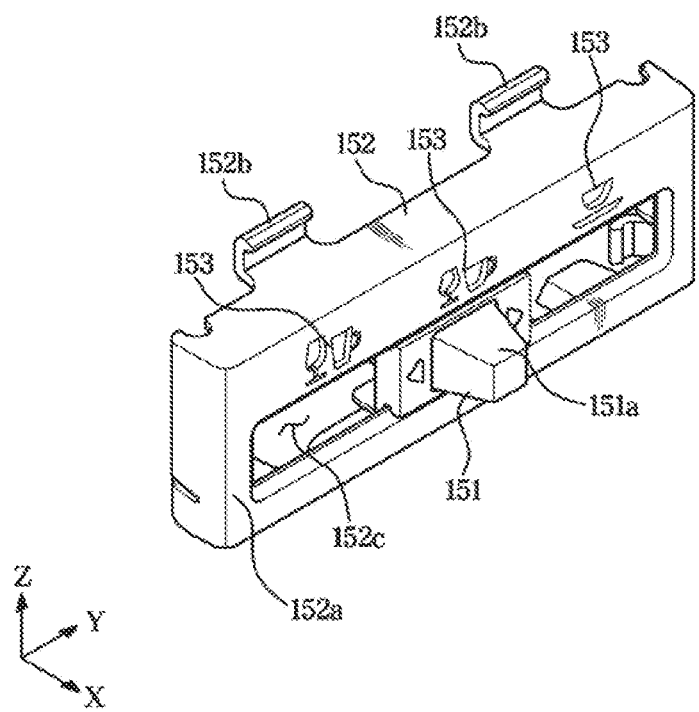
FIG. 9 is a perspective view illustrating a rotating device of the basket shown in FIG. 2.
Figure 10:
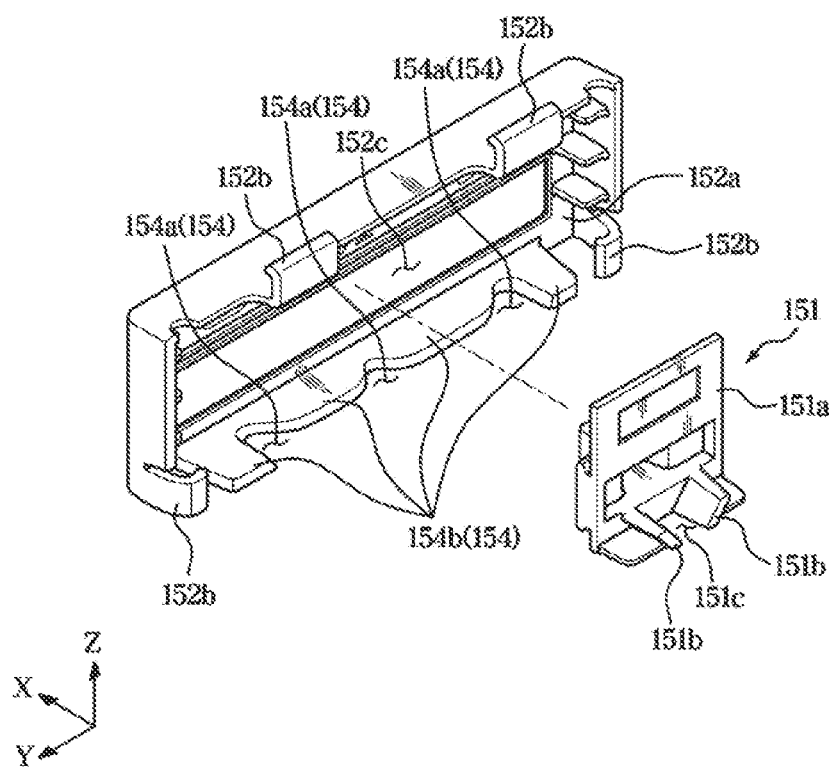
FIG. 10 is an exploded view of the rotating device shown in FIG. 9 as viewed from a rear side.

FIG. 2 is a perspective view illustrating a basket 100 of the dishwasher 1 shown in FIG. 1. FIG. 3 is a perspective view illustrating an upper holder frame 130 of the basket 100 shown in FIG. 2. FIG. 4 is a perspective view illustrating a lower holder frame 140 of the basket 100 shown in FIG. 2. FIG. 5 is a side view illustrating the lower holder frame 140 shown in FIG. 2. FIG. 6 is a front view illustrating the lower holder frame 140 shown in FIG. 2. FIG. 7 is a perspective view illustrating a binder 160 of the basket 100 shown in FIG. 2. FIG. 8 is a rear view illustrating a part of the basket 100 shown in FIG. 2. FIG. 9 is a perspective view illustrating a rotating device of the basket 100 shown in FIG. 2. FIG. 10 is an exploded view of the rotating device shown in FIG. 9 as viewed from a rear side.

Hereinafter the middle basket 100 will be described as an example. However, the disclosure is not limited thereto, and the following description may be applied to the lower basket and the upper basket.

Referring to FIGS. 2 to 10, the basket 100 may include a substantially rectangular bottom surface and a basket body 110 including a front surface, a rear surface, a left surface, and a right surface surrounding four corners of the bottom surface. The basket body 110 forms the exterior of the basket 100, and dishes may be accommodated in the basket body 110. The basket body 110 may be formed with a plurality of wires. Particularly, the basket body 110 may have a wire basket shape in which a plurality of wires is combined in a grid shape.

The basket body 110 may include a plurality of holding grooves 111 on which dishes such as plates may be held. The plurality of holding grooves 111 may be formed by wires forming the basket body 110.

The basket 100 may include a roller assembly 120 fixed to opposite sides of the basket body 110 and a movement of the roller assembly 120 may be guided by the guide rack 13a in response to the basket 100 being inserted into the rack.

The basket 100 may include holder frames 130 and 140 provided to hold dishes including wine glasses and the like.

The basket 100 may include an upper holder frame 130 provided to hold dishes.

The upper holder frame 130 may include a first frame body 131, a holding tine 133, and a coupling tine 132. The first frame body 131, the holding tine 133, and the coupling tine 132 may each be provided in plurality.

The first frame body 131 may have a bar shape extending in the front and rear direction X. The coupling tine 132 may be connected to one end of the first frame body 131. The holding tine 133 may be connected to the first frame body 131 and may protrude from the first frame body 131.

One side of the upper holder frame 130 may be rotatably coupled to the basket body 110. Particularly, on one surface of the basket body 110, a rotating shaft 112 of the upper holder frame 130 may be formed to protrude inward of the basket body 110, and the coupling tine 132 may include a shaft insertion member 132a. As the rotating shaft 112 of the basket body 110 is inserted into the shaft insertion member 132a of the coupling tine 132, the upper holder frame 130 may be rotatably coupled to the basket body 110. A stopper (not shown) arranged under the upper holder frame 130 to support the upper holder frame 130 and provided to limit a rotation range of the upper holder frame to prevent the upper holder frame 130 from being sagged or rotated below a certain range may be provided in the basket body 110.

In the basket 100 shown in FIG. 2, it is illustrated that the upper holder frame 130 is coupled to the front and rear surfaces of the basket body 110 but is not limited thereto. Alternatively, the upper holder frame 130 may be coupled to left and right surfaces of the basket body 110, or the upper holder frame 130 may be coupled to one of the left and right surfaces and one of front and rear surfaces of the basket body 110. For another example, the rotating shaft may be formed on the coupling tine 132 and the shaft insertion member may be formed on the basket body 110.

Dishes may be held on the upper holder frame 130. Particularly, a wine glass may be held on the upper holder frame 130. Particularly, a stem of a wine glass or a base of a wine glass may be held on the upper holder frame 130.

The upper holder frame 130 may include a plurality of holding grooves 134 formed on the other side opposite to one side coupled to the basket body 110, so as to allow dishes to be held thereon. Particularly, the holding tine 133 protruding from the first frame body 131 toward a direction opposite to a rotation axis of the upper holder frame 130 may include the holding groove 134 that is formed by bending a portion of the holding tine 133. A stem or a base of a wine glass may be held on the holding groove 134 such that the ball of the wine glass faces downward.

The basket 100 may include the lower holder frame 140 provided to hold dishes.

The lower holder frame 140 may be rotatably coupled to the basket body 110. The lower holder frame 140 may be rotatably coupled to a bottom side of the basket body 110. Particularly, the lower holder frame 140 may be rotatably coupled to the basket body 110 by a binder 160 to be described later.

The lower holder frame 140 may include a second frame body 141, a support tine 142, and a connection tine 143.

The lower holder frame 140 may include the second frame body 141 to which the support tine 142 and the connection tine 143 are coupled. The second frame body 141 may have a bar shape extending in the front and rear direction X. The second frame body 141 may be rotatably coupled to the basket body 110 by the binder 160.

The lower holder frame 140 may include the support tine 142 supporting a wine glass. Particularly, the support tine 142 may support a ball of a wine glass held on the upper holder frame 130 so as to prevent the wine glass held on the upper hold frame 130 from shaking. The support tine 142 may be connected to the second frame body 141 and protrude from the second frame body 141. The support tine 142 may include a plurality of support tines 142. A gap between the two adjacent support tines 142 may correspond to a holding groove 144, and dishes such as a plate may be arranged and supported in the holding groove 144 formed between the two adjacent support tines 142. The holding groove 144 may include a plurality of holding grooves 144, and widths of the plurality of holding grooves 144 may be the same or different.

The support tine 142 may include a bending member 142a and a support member 142c. The bending member 142a may be provided in plurality. The plurality of bending members 142a may be arranged in a line to form a line including at least one bending point 142aa, and may be connected to each other in the arranged state. In other words, the support tine 142 may include a plurality of bending points 142aa. At this time, a portion of the support tine formed by the plurality of bending members 142a that is arranged and connected in one line may be referred to as an extension 142b. The plurality of bending members 142a may be arranged on one plane M. That is, the extension 142b including the plurality of bending points 142aa may lie on one plane M.

The support tine 142 may include the support member 142c in contact with a ball of a wine glass. The support member 142c may be connected to the second frame body 141 through the plurality of bending members 142a. In other words, the support member 142c may be connected to the second frame body through the extension 142b.

As mentioned above, as the support tine 142 includes the plurality of bending points 142aa, the support tine 142 may be provided in such a way that a curved surface thereof is in close contact with a surface of a plate or a portion of the curved surface is inserted into a concave bowl so as to more stably support dishes including a plate and a bowl.

The support member 142c may be bent at the extension 142b. Particularly, because the extension 142b is formed by connecting the plurality of bending members 142a, the extension 142b may lie on the plane M, on which the plurality of bending members 142a is arranged, and the support member 142c may be bent from other end of the extension 142b, which is opposite to one end of the extension 142b connected to the second frame body 141, to substantially upward Z so as not to lie on the plane M on which the plurality of bending members 142a is arranged. In other words, the support member 142c may be formed to protrude from the other end of the extension 142b toward a direction approaching the upper holder frame 130.

The lower holder frame 140 may include the connection tine 143 connected to a rotating device 150. The connection tine 143 may be connected to one end of the second frame body 141. The connection tine 143 may be pressed and rotated by the rotating device 150. An operation of the connection tine 143 and the rotating device 150 will be described later in detail.

When the lower holder frame 140 is viewed from the front side X, a straight line l passing through the connection tine 143 may form a predetermined angle β with the plane M, on which the extension 142b is arranged. In other words, the connection tine 143 may not lie on the plane M. The second frame body 141, the support tine 142, and the connection tine 143 may be integrally formed with each other.

The basket 100 may include the binder 160 provided to allow the lower holder frame 140 to be rotatably coupled to the basket body 110. Particularly, the binder 160 may allow the lower holder frame 140 to be rotatably coupled to the bottom of the basket body 110. The binder 160 may include a plurality of binders 160.

The binder 160 may include a binder body 161 in which a plurality of binding grooves 164 and 165 is formed, a clamp 162 formed in a lower portion of the binder body 161, and a connection member 163 connecting the binder body 161 and the clamp 162.

The plurality of binding grooves 164 and 165 may include a first binding groove 164 into which the second frame body 141 is inserted, and a second binding groove 165 into which one wire 110a of the wires forming the basket body 110 is inserted. Because the first binding groove 164 and the second binding groove 165 are parallel to each other, the wire 110a parallel to the second frame body 141 may be inserted into the second binding groove 165. The lower holder frame 140 in a state in which the second frame body 141 is inserted into the first binding groove 164 may be rotatable, and the second frame body 141 may form a rotation axis of the lower holder frame 140.

The clamp 162 may be coupled to one wire 110b of the wires forming the basket body 110. Particularly, the wire 110b perpendicular to the wire 110a inserted into the second binding groove 165 may be inserted into and coupled to a fastening space 162a between the binder body 161 and the clamp 162, and the binder 160 may be fixed to the basket body 110. The wire 110a inserted into the second binding groove 165 and the wire 110b inserted into the fastening space 162a may be included in the wires 110a and 110b forming the bottom of the basket body 110.

The binder 160 may be arranged behind the adjacent support tine 142. In other words, between the binder 160 and the support tine 142 adjacent to the binder 160, the binder 160 may be arranged closer to the rotating device 150. Particularly, the connection member 163 of the binder 160 may be arranged between the wire 110b inserted into the fastening space 162a of the binder 160 and the support tine 142 adjacent to the binder 160. However, the disclosure is not limited thereto, and the binder 160 may be arranged in front of the adjacent support tine 142.

Meanwhile, the connection tine 143 may be inclined toward the center of the second frame body 141 by a predetermined angle α with respect to a straight line perpendicular to the second frame body 141. Particularly, the connection tine 143 may be inclined at 3° with respect to a straight line perpendicular to the second frame body 141.

In addition, a step may be formed in a middle portion of the connection tine 143. Particularly, the connection tine 143 may include a first member 143a connected to one end of the second frame body 141 and extending to be inclined in the direction of the center of the frame body by a predetermined angle α with respect to the straight line perpendicular to the second frame body 141, a step member 143b bent at an end of the first member 143a toward a direction opposite to the inclined direction of the first member 143a and extending substantially parallel to the second frame body 141, and a second member 143c extending from an end of the step member 143b toward a direction away from the second frame body 141 to be approximately parallel to the first member 143*a* and then coupled to the rotating device 150.

In response to the connection tine 143 being coupled to the rotating device 150 in a state in which the lower holder frame 140 is coupled to the basket body 110 by the binder 160, the connection tine 143 may be pulled to a direction opposite to the inclined direction of the connection tine 143, and thus the connection tine 143 in an elastically deformed state may be coupled to the rotating device 150. At this time, by the elastic restoring force, the second frame body 141 connected to the connection tine 143 may be pulled in a rearward direction with respect to FIG. 2 by the connection tine 143. That is, the second frame body 141 may be pulled in a direction toward the rotating device 150.

In response to the second frame body 141 being pulled, the support tine 142 may be also moved. However, because the connection member 163 of the binder 160 is arranged between the adjacent support tine 142 and the wire 110*b* inserted into the fastening space 162*a*, the binder 160 may be prevented from being rearwardly moved by the support tine 142, and the movement of the support tine 142 may be limited by the binder 160. That is, even when the restoring force of the connection tine 143 acts, the support tine 142 and the second frame body 141 may not be moved in the direction toward the rotating device 150. In addition, because the binder 160 and the support tine 142 adjacent to the binder 160 are firmly fixed in contact with each other by the restoring force of the connection tine 143, the coupling of the binder 160, the basket body 110, and the lower holder frame 140 may be stronger.

The basket 100 may include the rotating device 150 configured to rotate the lower holder frame 140.

The rotating device 150 may include a slide button 151 to which one end of the connection tine 143 is coupled and provided to press the connection tine 143, and a rotating device body 152 coupled to the basket body 110 and including a guide rail 152*c* to which the slide button 151 is inserted and coupled.

The slide button 151 may include a button body 151*a* provided to be gripped by a user, and a coupling rib 151*b* protruding from a rear surface of the button body 151*a* to form a coupling groove 151*c*. One end of the connection tine 143 may be inserted and coupled into the coupling groove 151*c*. Particularly, the connection tine 143 may be arranged at a rear of the rotating device 150, and the connection tine 143 arranged at the rear of the rotating device 150 may be inserted into the coupling groove 151*c* located at the rear of the button body 151*a*.

The rotating device body 152 may include a plate-shaped body plate 152*a*, a plurality of couplers 152*b* protruding from the body plate 152*a* and coupled to the basket body 110, and the opening-shaped guide rail 152*c* formed on the body plate 152*a* and extending in the left and right direction Y. The slide button 151 may be inserted into the guide rail 152*c* and slid in the left and right direction Y along the guide rail 152*c*. The slide button 151 may be operated manually but is not limited thereto. Alternatively, the sliding button 151 may be automatically slid by a separate power source, controller, inputter, and power transmission mechanism.

As the slide button 151 slides, the slide button 151 may press the connection tine 143 connected to the slide button 151 in a sliding direction and may rotate the connection tine 143 in the direction of pressing the connection tine 143.

In response to the rotation of the connection tine 143, the second frame body 141 connected to the connection tine 143 and the support tine 142 connected to the second frame body 141 may also rotate together. In other words, by sliding the slide button 151 to a predetermined position, the lower holder frame 140 may be rotated to allow the support tine 142 to be positioned to correspond to dishes including a wine glass held on the upper holder frame 130.

The rotating device body 152 may include an indicator 153 provided on a front surface of the rotating device body 152. When the slide button 151 reaches a position in which the indicator 153 is placed, the lower holder frame 140 may be rotated and the indicator 153 may indicate the size of wine glass or cup corresponding to the lower holder frame 140. The indicator 153 may be arranged above the guide rail 152*c*.

The indicator 153 may include the shape of dishes including a wine glass, a cup, and the like, and the indicator 153 may be provided in plurality. The indicator 153 may be displayed in the rotating device body 152 in such a way that the indicator 153 is printed, embossed or engraved on the front surface of the body plate 152*a*, and a portion of the body plate 152*a* is cut out such as a stencil plate. However, the disclosure is not limited thereto, and the indicator 153 may be provided on the rotating device body 152 in various ways.

The rotating device body 152 may include a mounting rib 154 protruding backward from the rear surface of the body plate 152*a*, and including a plurality of mounting grooves 154*a* to which the connection tine 143 rotated by the slide button 151 is mounted.

The mounting rib 154 may include the plurality of mounting grooves 154*a* and a rib 154*b* between two adjacent mounting grooves 154*a*. In other words, the mounting groove 154*a* may correspond to a space between two adjacent rib 154*b*. The plurality of mounting grooves 154*a* may correspond one by one to the indicator 153. Accordingly, the mounting groove 154*a* may be arranged under the corresponding indicator 153.

A side end of the rib 154*b* may be rounded to have a curved shape to allow the connection tine 143 to escape from the mounting groove 154*a* when the connection tine 143 mounted to one mounting groove 154*a* starts to move to another mounting groove 154*a* by the slide button 151.

The rib 154*b* may protrude further rearward than the mounting groove 154*a*, and thus a degree of deformation of the connection tine 143 placed at the rib 154*b* may be greater than the connection tine 143 placed at the mounting groove 154*a*. Accordingly, an additional force for elastic deformation of the connection tine 143 may be required to move the connection tine 143, which is mounted on the mounting groove 154*a*, to the rib 154*b*, and thus even when a rotational force caused by a weight of the dishes is transmitted to the connection tine 143 through the support tine 142 and the second frame body 141, it is difficult for the connection tine 143 to be easily separated from the mounting groove 154*a* and to be moved to the rib 154*b*.

Therefore, when the connection tine 143 is mounted on the mounting groove 154*a*, it is possible to prevent that the lower holder frame 140 is unintentionally rotated by the weight of dishes such as wine glasses, and accordingly, it is also possible to prevent unintentional movement of the connection tine 143 and the slide button 151.

Figure 11:
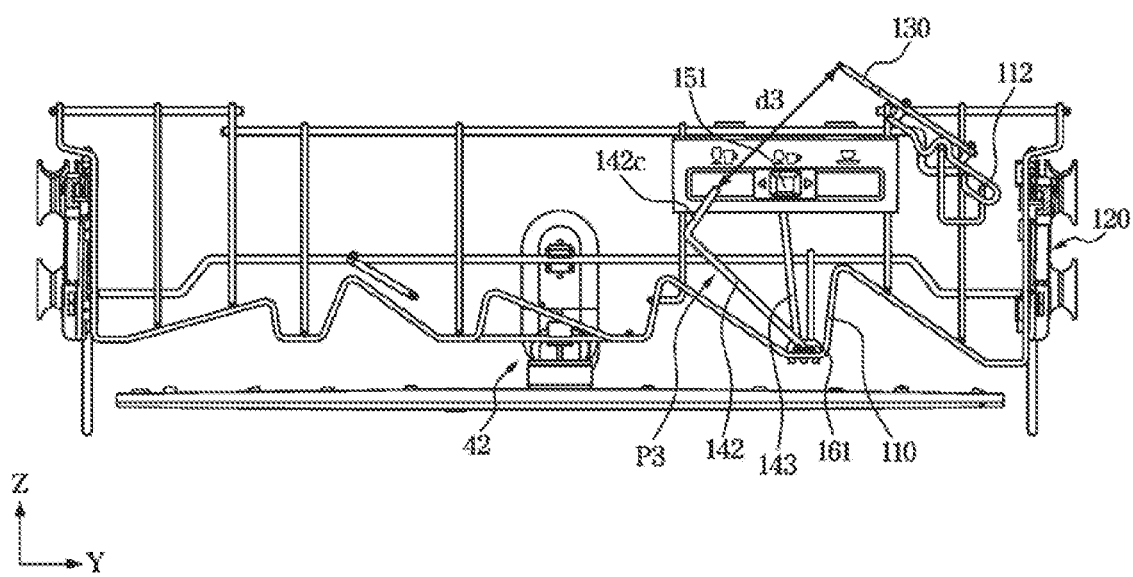
FIG. 11 is a cross-sectional view taken along a line XI-XI' when the lower holder frame of the basket shown in FIG. 2 is at a third position.
Figure 12:
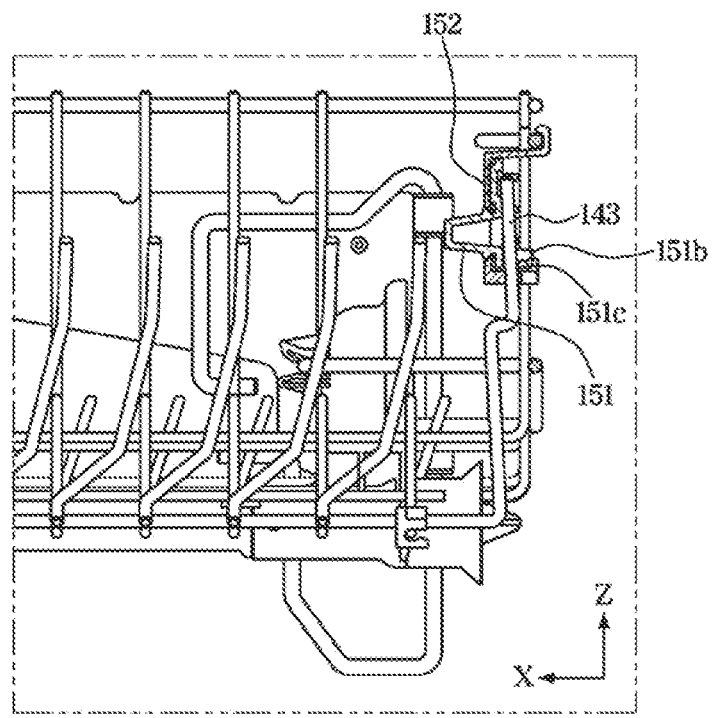
FIG. 12 is a cross-sectional view taken along a line XII-XII' when the lower holder frame of the basket shown in FIG. 2 is at the third position.
Figure 13:
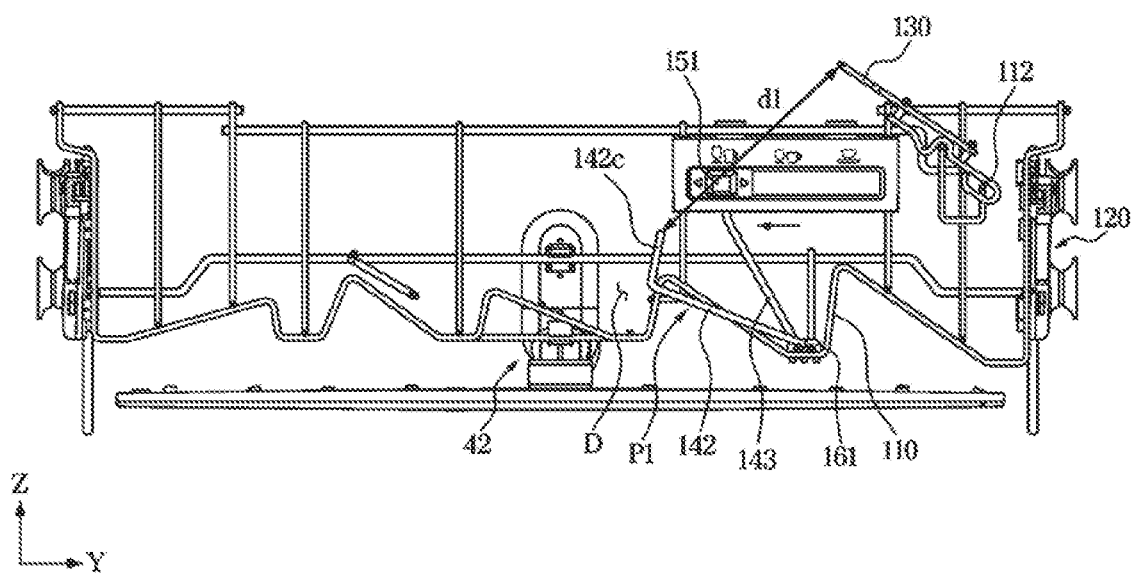
FIG. 13 is a cross-sectional view taken along the line XI-XI' when the lower holder frame of the basket shown in FIG. 2 is at a first position.
Figure 14:
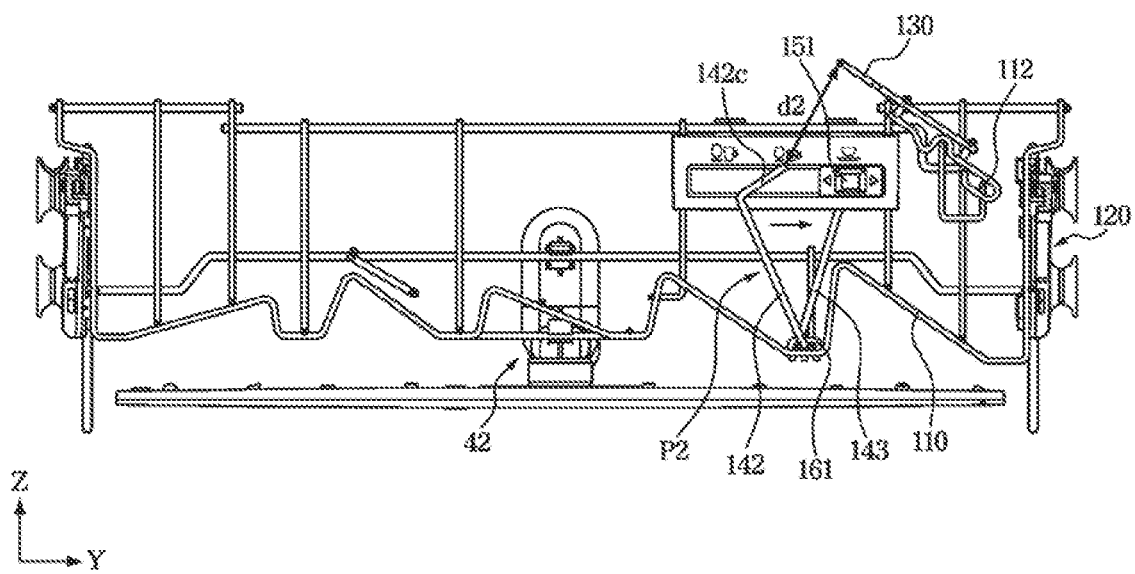
FIG. 14 is a cross-sectional view taken along the line XI-XI' when the lower holder frame of the basket shown in FIG. 2 is at a second position.
Figure 15:
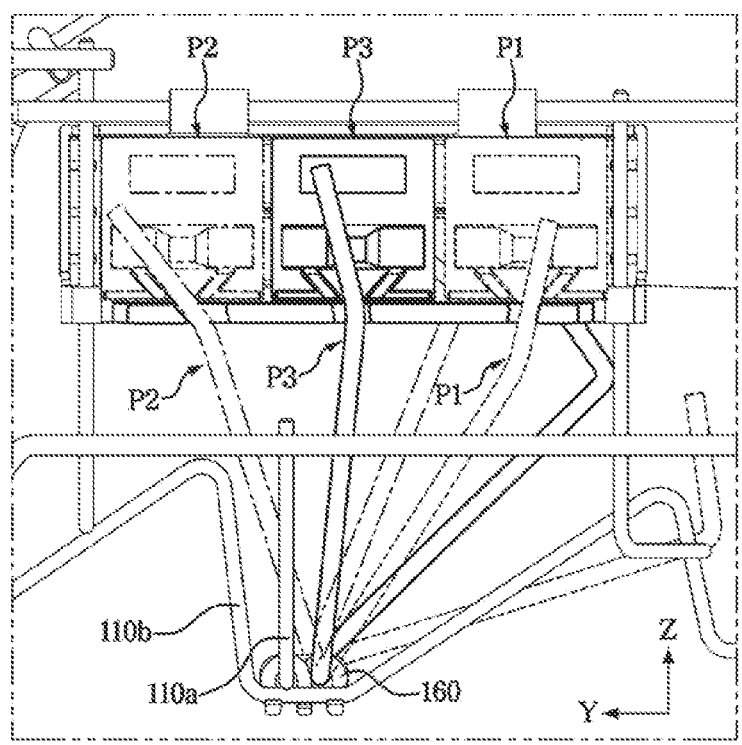
FIG. 15 is a view illustrating a state in which a slide button is at the first position, the second position, and the third position in the basket shown in FIG. 2.

FIG. 11 is a cross-sectional view taken along a line XI-XI' when the lower holder frame 140 of the basket 100 shown in FIG. 2 is at a third position P3. FIG. 12 is a cross-sectional view taken along a line XII-XII' when the lower holder frame 140 of the basket 100 shown in FIG. 2 is at the third position P3. FIG. 13 is a cross-sectional view taken along the line XI-XI' when the lower holder frame 140 of the basket 100 shown in FIG. 2 is at a first position P1. FIG. 14 is a cross-sectional view taken along the line XI-XI' when the lower holder frame 140 of the basket 100 shown in FIG. 2 is at a second position P2. FIG. 15 is a view illustrating a state in which a slide button 151 is at the first position P1, the second position P2, and the third position P3 in the basket 100 shown in FIG. 2.

Referring to FIGS. 11 to 15, a state in which the slide button 151 is moved to a leftmost position inside the guide rail 152*c* may be referred to as a first position P1, a state in which the slide button 151 is moved to a rightmost position may be referred to a second position P2, and a state in which the slide button 151 is approximately at a center of the guide rail 152*c* may be referred to a third position P3.

Further, a position of the lower holder frame 140 and a position of the support tine 142 when the slide button 151 is placed at the first position P1 may be referred to as the first position P1. A position of the lower holder frame 140 and a position of the support tine 142 when the slide button 151 is paced at the second position P2 may be referred to as the second position P2. A position of the lower holder frame 140 and a position of the support tine 142 when the slide button 151 is paced at the third position P3 may be referred to as the third position P3.

However, the disclosure is not limited thereto, and the slide button 151 may be positioned only at the first position P1 or the second position P2, or may be positioned at various positions between the first position P1 and the second position P2 according to the purpose of the manufacturer and the user.

In response to the slide button 151 being positioned at the first position P1, a distance between one end of the lower holder frame 140 and one end of the upper holder frame 130 that support dishes is increased in comparison with the state of being positioned at the second position P2 or the third position P3. Particularly, in response to the slide button 151 being positioned at the first position P1, a distance between one end of the holding tine 133, in which the holding groove 134, on which the dish is held, is formed, and one end of the support member 142*c* of the support tine 142 supporting the dish held on the holding groove 134 is increased in comparison with the state of being positioned at the second position P2 or the third position P3. In other words, the support tine 142 of the lower holder frame 140 being positioned at the first position P1 may be closer to the bottom of the basket body 110 in comparison with the second position P2 or the third position P3. At this time, a distance between one end of the support member 142*c* and one end of the holding tine 133 may be referred to as a first distance d1.

Accordingly, in response to the lower holder frame 140 being positioned at the first position P1, dishes such as a large wine glass may be stably held between the lower holder frame 140 and the upper holder frame 130. In addition, in a side region D of the support member 142*c* of the lower holder frame 140, a side surface of dishes such as cups placed on the bottom of the basket body 110 may be supported by the support member 142*c*, thereby being stably placed in the basket body 110.

In response to the slide button 151 being positioned at the second position P2, the distance between one end of the lower holder frame 140 and one end of the upper holder frame 130 that support dishes is reduced in comparison with the state of being positioned at the first position P1 or the third position P3. Particularly, in response to the slide button 151 being positioned at the second position P2, a distance between one end of the holding tine 133, in which the holding groove 134, on which the dish is held, is formed, and one end of the support member 142*c* of the support tine 142 supporting the dish held on the holding groove 134 is reduced in comparison with the state of being positioned at the first position P1 or the third position P3. In other words, the support tine 142 of the lower holder frame 140 being positioned at the second position P2 may be further from the bottom of the basket body 110 in comparison with the first position P1 or the third position P3. At this time, a distance between one end of the support member 142*c* and one end of the holding tine 133 may be referred to as a second distance d2.

Therefore, in response to the lower holder frame 140 being positioned at the second position P2, dishes such as a small wine glass may be stably held between the lower holder frame 140 and the upper holder frame 130. In addition, dishes such as plates may be arranged and supported in the holding groove 144 between the support tines 142.

In response to the slide button 151 being positioned at the third position P3, the distance between one end of the lower holder frame 140 and one end of the upper holder frame 130 which support dishes is less than the state of being positioned at the first position P1 and greater than the state of being positioned at the second position P2. Particularly, in response to the slide button 151 being positioned at the third position P3, a distance between one end of the holding tine 133, in which the holding groove 134, on which the dish is held, is formed, and one end of the support member 142*c* of the support tine 142 supporting the dish held on the holding groove 134 is less than the state of being positioned at the first position P1 and greater than the state of being positioned at the second position P2. In other words, the support tine 142 of the lower holder frame 140 being positioned at the third position P3 may be further from the bottom of the basket body 110 in comparison with the first position P1 and may be closer to the bottom of the basket body 110 in comparison with the second position P2. At this time, a distance between one end of the support member 142*c* and one end of the holding tine 133 may be referred to as a third distance d3.

Therefore, in response to the lower holder frame 140 being positioned at the third position P3, medium-sized dishes such as a wine glass or cup may be stably supported between the lower holder frame 140 and the upper holder frame 130.

As described above, by operating the slide button 151 to be positioned at one of the first position P1, the second position P2, and the third position P3, it is possible to adjust the rotation of the lower holder frame 140, and it is possible to arrange the lower holder frame 140 according to dishes held on the upper holder frame 130. In other words, by operating the slide button 151 to be positioned at one of the first position P1, the second position P2, and the third position P3, it is possible to adjust the rotation of the lower holder frame 140, and it is possible to adjust the distance between one end of the lower holder frame 140 and one end of the upper holder frame 130.

However, the disclosure is not limited thereto, and the distance between one end of the lower holder frame 140 and one end of the upper holder frame 130 may be adjusted by the rotation of the upper holder frame 130. Because the upper holder frame 130 is rotatably provided on the basket body 110 as described above, the distance between one end of the upper holder frame 130 and one end of the lower holder frame 140 may vary according to the degree of rotation. Particularly, the upper holder frame 130 may be rotated from a position, in which a downward rotation of the upper holder frame 130 is limited by the stopper, to a position, in which the upper holder frame 130 is perpendicular to the ground. As the upper holder frame 130 is positioned at arbitrary position between the position, in which the downward rotation of the upper holder frame 130 is limited by the stopper, and the position, in which the upper holder frame 130 is perpendicular to the ground, the distance between one end of the support member 142c of the lower holder frame 140 and one end of the holding tine 133 of the upper holder frame 130 may be adjusted.

In this case, the lower holder frame 140 may be stationary or may be rotated by the rotating device 150. The upper holder frame 130 may include a separate connection tine connected to the first frame body 131 and an additional rotating device coupled to the connection tine.

Figure 16:
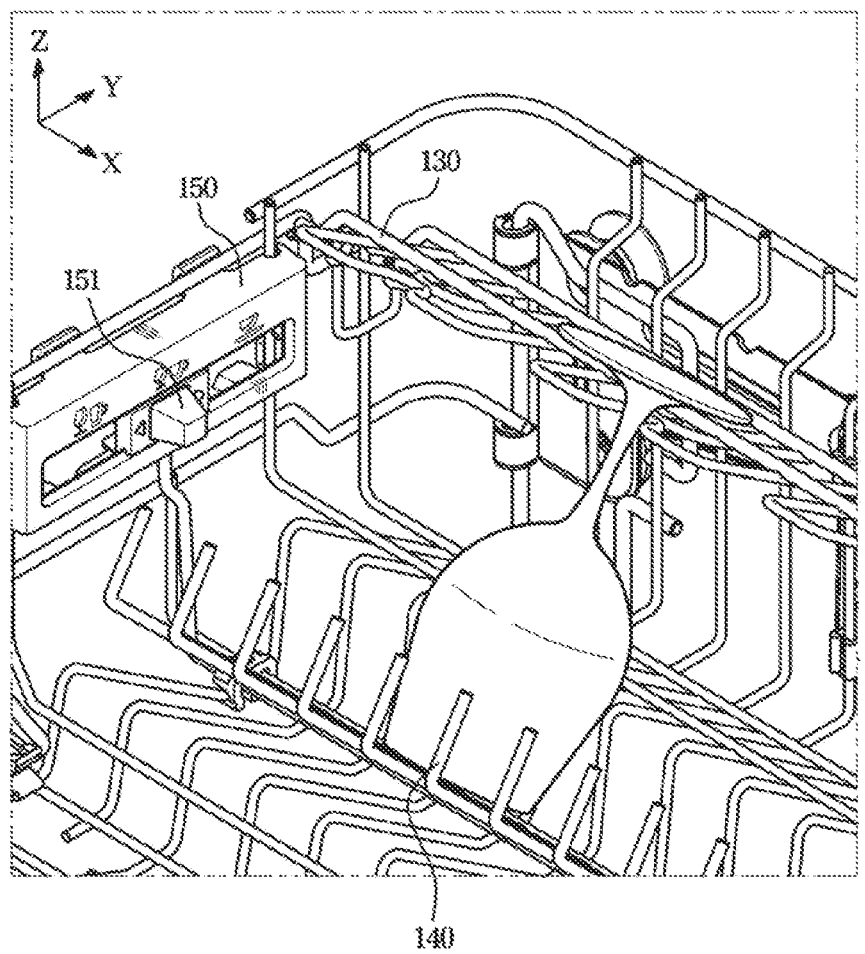
FIG. 16 is a view illustrating a state in which dishes are held when the lower holder frame of the basket shown in FIG. 2 is at the third position.
Figure 17:
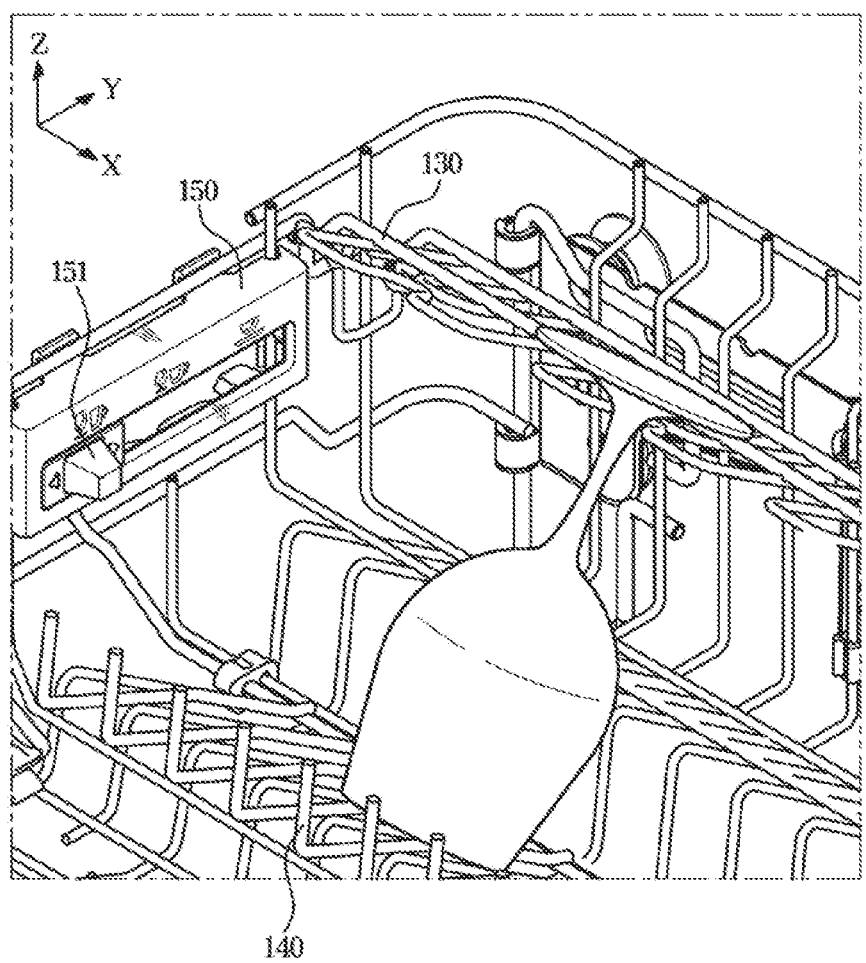
FIG. 17 is a view illustrating a state in which dishes are held when the lower holder frame of the basket shown in FIG. 2 is at the first position.
Figure 18:
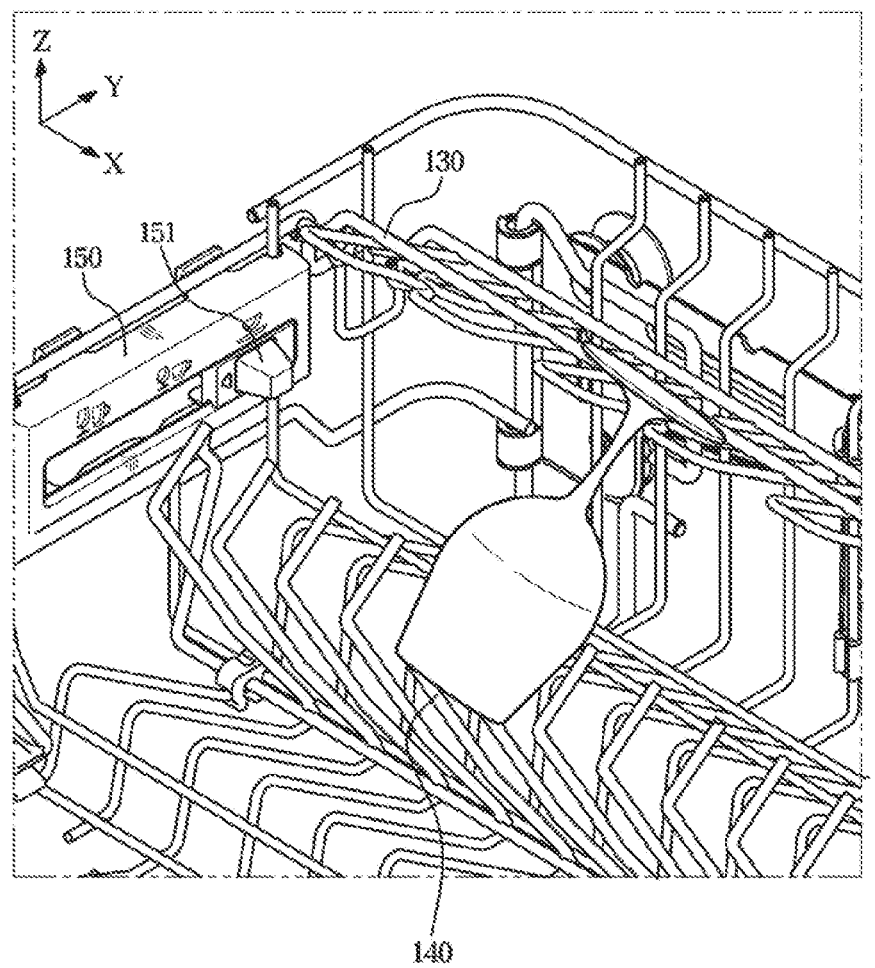
FIG. 18 is a view illustrating a state in which dishes are held when the lower holder frame of the basket shown in FIG. 2 is at the second position.

FIG. 16 is a view illustrating a state in which dishes are held when the lower holder frame 140 of the basket 100 shown in FIG. 2 is at the third position P3. FIG. 17 is a view illustrating a state in which dishes are held when the lower holder frame 140 of the basket 100 shown in FIG. 2 is at the first position P1. FIG. 18 is a view illustrating a state in which dishes are held when the lower holder frame 140 of the basket 100 shown in FIG. 2 is at the second position P2.

FIGS. 16 to 18 illustrate a state in which a wine glass is supported, but this is merely exemplary. Alternatively, other dishes including cups and the like may be supported, and a larger number of dishes may be supported. In addition, as for a wine glass, the support member 142c of the support tine 142 may be in contact with an inner surface of a ball of the wine glass to support the wine glass, or may be in contact with an outer surface of the ball of the wine glass to support the wine glass.

As is apparent from the above description, a dishwasher may include a lower holder frame including a plurality of support tines, so as to stably support dishes.

Further, because a position of a lower holder frame is adjusted according to the type and size of dishes, a dishwasher may support the dishes having various types and sizes.

Although a few embodiments of the disclosure have been shown and described, it would be appreciated by those skilled in the art that changes may be made in these embodiments without departing from the principles and spirit of the disclosure, the scope of which is defined in the claims and their equivalents.

Although the present disclosure has been described with various embodiments, various changes and modifications may be suggested to one skilled in the art. It is intended that the present disclosure encompass such changes and modifications as fall within the scope of the appended claims.

What is claimed is:

1. A dishwasher comprising:
a basket provided to accommodate dishes,
wherein the basket comprises:
a basket body;
an upper holder frame comprising one end supporting a portion of a dish, and an other end rotatably coupled to the basket body;
a lower holder frame comprising one end supporting an other portion of the dish supported by the upper holder frame, and an other end rotatably coupled to the basket body, and a frame body rotatably coupled to the basket body and extending in one direction; and
a rotating device fixed to the basket body and configured to rotate the lower holder frame; and
wherein a distance between the one end of the upper holder frame and the one end of the lower holder frame is adjusted as one of the upper holder frame and the lower holder frame is rotated, and
wherein the lower holder frame is bent at one end of the frame body to form a connection tine, wherein the connection tine is connected to the rotating device, and the connection tine is coupled to the rotating device,
wherein the rotating device comprises:
a slide button to which one end of the connection tine is coupled; and
a rotating device body coupled to the basket body and comprising a guide rail to which the slide button is inserted and coupled,
wherein, the slide button is configured to slide linearly against the rotating device body along the guide rail, and
in response to sliding the slide button linearly in one direction to adjust a distance between one end of the upper holder frame and a plurality of support tines, the slide button is configured to press the connection tine in one direction, the frame body is rotated by a pressure of the connection tine, and the plurality of support tines is rotated together with the frame body.

2. The dishwasher of claim 1, wherein:
the slide button comprises a coupling rib forming a coupling groove to which one end of the connection tine is inserted and coupled, and
the rotating device body comprises a mounting rib in which a plurality of mounting grooves is formed to allow the connection tine, which is rotated by the slide button, to be mounted thereto.

3. The dishwasher of claim 2, wherein:
the slide button is manually slidable, and
in response to fully sliding the slide button, the connection tine is mounted to one of the plurality of mounting grooves to prevent rotation of the lower holder caused by a weight of the dish.

4. The dishwasher of claim 1, wherein the lower holder frame comprises:
a plurality of support tines protruding from the frame body to support the dish and arranged in an extending direction of the frame body.

5. The dishwasher of claim 4, wherein each of the plurality of support tines comprises:
a support member in contact with the dish to support the dish; and
a plurality of bending members configured to connect the support member and the frame body, the plurality of bending members arranged to form a line comprising at least one bending point, the plurality of bending members connected to each other.

6. The dishwasher of claim 5, wherein:
the plurality of bending members is arranged to lie on one plane, and
the support member is bent at one end of the line formed by connecting the plurality of bending members to each other, so as not to lie on the plane.

7. The dishwasher of claim 4, wherein the basket further comprises a rotating device fixed to the basket body and configured to rotate the lower holder frame.

8. The dishwasher of claim 7, wherein:
the lower holder frame further comprises a connection tine bent at one end of the frame body and connected to the rotating device, and
the connection tine is coupled to the rotating device.

9. The dishwasher of claim 4, wherein the basket further comprises a binder provided to allow the lower holder frame to be rotatably coupled to the basket body.

10. The dishwasher of claim 9, wherein:
the basket body is formed in such a way that a plurality of wires is coupled to each other to form a grid shape, and
the binder comprises:
a first binding groove into which a frame body is inserted;
a second binding groove into which one of the plurality of wires parallel to the frame body is inserted; and
a clamp fastened to one of the plurality of wires perpendicular to one wire of the basket body inserted into the second binding groove.

11. The dishwasher of claim 4, wherein:
the frame body corresponds to a first frame body, and
the upper holder frame comprises:
a second frame body extending in one direction;
a coupling tine connected to a side end of the second frame body and rotatably coupled to the basket body; and
a holding tine protruding from the second frame body and forming a plurality of holding grooves supporting the dish.

12. The dishwasher of claim 11, wherein:
the dish comprises a wine glass,
a holding groove of the upper holder frame is configured to support a stem or a base of the wine glass; and
a support tine of the lower holder frame supports a ball of the wine glass.

13. The dishwasher of claim 4, wherein a wine glass is arranged and supported between a plurality of support tines.

14. A dishwasher including:
a washing chamber;
a basket body arranged inside the washing chamber to accommodate dishes; and
a holder frame including:
a frame body rotatably coupled to the basket body and extending in one direction,
a rotating device fixed to the basket body and configured to rotate the holder frame,
a plurality of support tines arranged to support the dishes and configured to rotate with respect to the basket body,
wherein the plurality of support tines is positioned at a first position or a second position according to a rotation of the holder frame,
wherein, in response to the plurality of support tines positioned in the first position, the plurality of support tines is arranged proximate to a bottom of the basket body to support the dishes placed on the basket body,
wherein, in response to the plurality of support tines positioned in the second position, the plurality of support tines is arranged further from the bottom of the basket body in comparison with the first position to allow the dishes to be supported between the plurality of support tines,
wherein the lower holder frame is bent at one end of the frame body to form a connection tine, and wherein the connection tine is connected to the rotating device, and the connection tine is coupled to the rotating device, and
wherein the rotating device comprises:
a slide button configured to slide to press a connection tine, and
a rotating device body including a guide rail provided to guide a linear sliding of the slide button.

15. The dishwasher of claim 14, wherein the plurality of support tines protruding from the frame body.

16. The dishwasher of claim 15, wherein each of the plurality of support tines includes:
an extension member extending from the frame body in one direction, and
a support member bent at one end of the extension to support the dishes in response to the plurality of support tines being positioned at the first position.

17. The dishwasher of claim 14, wherein:
the holder frame corresponds to a first holder frame,
the dishwasher further includes a second holder frame rotatably coupled to the basket body and configured to support the dishes, and
one portion of a dish is supported by the first holder frame and an other portion of the dish is supported by the second holder frame.

18. The dishwasher of claim 14, wherein the rotating device comprises:
a slide button configured to slide to press a connection tine, and
a rotating device body including a guide rail provided to guide a sliding of the slide button.

* * * * *